United States Patent
Mikkelsen et al.

(10) Patent No.: US 8,581,194 B2
(45) Date of Patent: Nov. 12, 2013

(54) METHOD AND APPARATUS FOR MEASURING A SPECTRUM OF AN OPTICAL SENSOR, ADVANTAGEOUSLY IN THE INFRARED REGION

(75) Inventors: Hakon Mikkelsen, Aldenhoven (DE); Ralf Bernhard, Stuttgart (DE)

(73) Assignee: Endres + Hauser Conducta Gesellschaft für Mess-und Regeltechnik + Co. KG, Gerlingen (DE)

( * ) Notice: Subject to any disclaimer, the term of this patent is extended or adjusted under 35 U.S.C. 154(b) by 37 days.

(21) Appl. No.: 13/324,447

(22) Filed: Dec. 13, 2011

(65) Prior Publication Data
US 2012/0153158 A1 Jun. 21, 2012

(30) Foreign Application Priority Data

Dec. 20, 2010 (DE) .................. 10 2010 063 533

(51) Int. Cl.
*G01J 5/02* (2006.01)
(52) U.S. Cl.
USPC .................................... 250/339.07
(58) Field of Classification Search
USPC ......... 250/339.01–339.15, 338.1–338.5, 340, 250/341.1–341.8, 342–352
See application file for complete search history.

(56) References Cited

U.S. PATENT DOCUMENTS

| | | | | |
|---|---|---|---|---|
| 3,803,384 A | * | 4/1974 | Braunlich | 250/345 |
| 5,153,771 A | * | 10/1992 | Link et al. | 359/286 |
| 5,315,434 A | * | 5/1994 | Mizuno et al. | 359/355 |
| 5,646,729 A | * | 7/1997 | Koskinen et al. | 356/454 |
| 5,694,930 A | | 12/1997 | Pries et al. | |
| 7,356,364 B1 | * | 4/2008 | Bullock et al. | 600/310 |
| 7,812,312 B2 | * | 10/2010 | Mantele et al. | 250/343 |
| 8,322,191 B2 | * | 12/2012 | Fritz | 73/24.02 |
| 2007/0191696 A1 | | 8/2007 | Mischler et al. | |
| 2007/0273867 A1 | | 11/2007 | Diessel et al. | |

FOREIGN PATENT DOCUMENTS

| | | |
|---|---|---|
| DE | 4227813 A1 | 2/1994 |
| DE | 10328998 A1 | 1/2005 |
| GB | 1294176 | 10/1972 |
| JP | 20011174405 A | 6/2001 |

OTHER PUBLICATIONS

German Search Report dated Sep. 14, 2011.

* cited by examiner

*Primary Examiner* — Kiho Kim
(74) *Attorney, Agent, or Firm* — Bacon & Thomas, PLLC

(57) ABSTRACT

A method for measuring a spectrum of an optical sensor, advantageously in the infrared region, in which a light beam impinges on an optical sensor in contact with a medium to be measured, wherein the optical sensor transmits a measurement beam changed by the medium to be measured and the measurement beam is fed to a pyrodetector, which issues output signals corresponding to the spectrum. The intensity of the measurement signal is modulated before impinging on a pyrodetector. In order to provide a cost effective, vibration free measuring apparatus, which has a long lifetime, intensity modulation of measurement beam occurs by tuning-in wavelengths contained in the optical spectrum of measuring beam.

10 Claims, 3 Drawing Sheets

METHOD AND APPARATUS FOR MEASURING A SPECTRUM OF AN OPTICAL SENSOR, ADVANTAGEOUSLY IN THE INFRARED REGION

TECHNICAL FIELD

The invention relates to a method for measuring a spectrum of an optical sensor, advantageously in the infrared region, in which a light beam impinges on an optical sensor, which is in contact with a medium to be measured, wherein the optical sensor transmits a measurement beam changed by the medium to be measured and the measurement beam is fed to a pyrodetector, which issues output signals corresponding to the spectrum; wherein the intensity of the measurement signal is modulated before impinging on the pyrodetector. The invention also relates to an apparatus for performing the method.

BACKGROUND DISCUSSION

Many applications for process spectrometers to measure concentrations of measured objects are found in the field of middle infrared radiation (MIR) and, respectively, infrared radiation (IR). These applications are found in the chemical industry, as well as in the fields of food or drink production, or in the pharmaceuticals industry. Pyrodetectors are frequently used for cost effective detection of light in the middle infrared and, respectively, the infrared spectral ranges. These pyrodetectors react to differences in the thermal warming of a sensor element. Therefore, the intensity of the light to be measured is usually modulated in order to obtain an alternating voltage signal at the output of the pyrodetector; the amplitude of the alternating voltage signal is a measure of the absolute intensity to be measured.

Different options are available to obtain such an alternating signal: in the case of mechanical modulation, the beam path is continuously interrupted before the pyrodetector, for example, by using a rotating chopper wheel. This solution leads to significant mechanical complexity and to susceptibilities as regards the mechanical wear of the rotating chopper wheel. Moreover, the dimensions of the spectrometer are enlarged by having to contain the chopper wheel and the pyrodetector.

Another possibility is electrical modulation, in which light from a light source, which transmits a light beam to an optical sensor, is electrically modulated. The light beam received by the optical sensor is changed by a medium to be measured and fed as a measurement signal to the pyrodetector. The electrical modulation also occurs before the light impinges on the pyrodetector in this case. The electrical modulation has the disadvantage that a decreasing modulation depth arises with increasing frequency because of the thermal mass of the light source being used. Moreover, the lifetime of the light source is limited by the temperature cycles, so that a new adjustment of the pyrodetectors must occur in replacing the light source.

SUMMARY OF THE INVENTION

An object of the invention is to provide a method, in which cost effective measurement of infrared spectra is possible using a pyrodetector, wherein a large spectral range is covered by a measurement setup, which is insensitive to vibration as well as being long lived.

According to the invention, the object is achieved in that the intensity modulation of the measuring beam occurs by tuning-in wavelengths contained in the optical spectrum of the measurement beam. Since the pyrodetector reacts to changing intensities of the measurement signal, these changing intensities are brought about according to the present invention indirectly by time sequenced tuning-in of different wavelengths of the spectrum of the measurement beam, wherein each wavelength of the optical spectrum of the measurement signal has a different intensity. Thus, simply, a spectrally resolved detection of the wavelength range of the measurement signal using a cost effective pyrodetector is possible. This has the advantage that no mechanical modulation for changing the intensity of the measurement signal over time is required, which enables an especially stable and insusceptible construction of the measurement setup. This measuring method is very long lived, since an electrical modulation of the transmitted light beam is omitted.

Advantageously, the light beam is transmitted free of modulation. Such a static signal from the light source increases the lifetime of the light source, since it is not subjected to temperature cycles.

In a further development, either only a narrow first region surrounding a wavelength of the optical spectrum to be detected or a wider second region surrounding a wavelength of the optical spectrum to be detected is tuned through. A differentiated spectrum of the measurement signal of the optical sensor is especially reached with the application of the modulation over the wavelengths of a large spectral region; the absolute spectrum of the measurement signal results from the differentiated spectrum through, except for an integration constant.

In a further development, a difference is determined from the intensities of two wavelengths measured by the pyrodetector; a determination of an integration constant is based on the difference. Such a difference measurement of the intensities can be created from two neighboring wavelengths or two wavelengths widely remote from one another. In such case, electronic modulation rapidly switches back and forth between two wavelengths. The resulting signal strengths, which the pyrodetector issues as an output signal, is a measure of the intensity difference of the two wavelengths. Through evaluation of the phase of the measurement signal, it can be determined which of the two wavelengths has the higher intensity, from which the integration constant is ascertained.

In a variant, a position with zero intensity is produced in the spectrum of the measurement beam. This position with zero intensity is utilized as a reference point for measuring the wavelengths in the optical spectrum of the measurement signal. Since no measurement signal reaches the pyrodetector at this position, the position of zero intensity forms the starting point for the measured spectrum.

In order to obtain a second reference point for measuring the optical spectrum of the measurement signal, a narrow band reference signal impinges on the pyrodetector, preferably simultaneously with the measurement beam. In this way, a very narrow band of light reaches the detector for the wavelength used as the reference signal. Since this marked region in the measuring light partially fills the point with zero intensity and the wavelength of the reference signal is known, thus, a second reference point is known, in order to associate the intensity curve of the wave length marking.

In an especially simple embodiment, the reference signal is an additional light beam, which is bandpass filtered before impinging on the pyrodetector. This has the advantage that a very cost effective white light source can be utilized in the measuring arrangement.

Another further development of the invention relates to an apparatus for measuring a spectrum of an optical sensor, advantageously in the infrared region, in which a light beam transmitted by a light source impinges on an optical sensor in contact with a medium to be measured, wherein the optical sensor transmits a measurement beam changed by the medium to be measured; the measurement beam is fed to a pyrodetector, which issues an output signal corresponding to the spectrum; wherein an intensity modulator, which changes the intensity of the measuring beam, is arranged before the pyrodetector. In order to realize a measuring arrangement, which is not only price favorable but also insensitive to vibration and long lived, the intensity modulator comprises a filter with a tunable wavelength. With the help of this filter, the measurement signal is decomposed into a wavelength spectrum, wherein the filter continually tunes-in individual wavelengths, which are contained in this wavelength spectrum. Since each wavelength has a different intensity in the optical spectrum, different intensities, which impinge on the pyrodetector, are indirectly produced in this manner, wherein the pyrodetector issues a corresponding output signal due to the changing intensities; the output signal decomposes the measurement beam spectrally. Thus, vibration sensitive, mechanical arrangements do not need to be used for creation of an alternating signal for the pyrodetector.

In an embodiment, the filter is embodied as a Fabry-Perot filter, which is arranged within the spectrometer either before the pyrodetector or together with the pyrodetector. Especially when the spectrometer comprises all needed components, such as the electrically tunable Fabry-Perot filter and the pyrodetector, a relatively small and easily manageable spectrometer is possible as a measuring arrangement. In spite of this, such a spectrometer covers a large spectral range, which has the advantage that a sufficiently good discrimination between different materials to be examined is possible.

In a variant, a notch filter, a shortpass filter or a longpass filter is arranged in the measurement beam before the spectrometer. These different filter types enable the production of the reference point with zero intensity. A notch filter is a narrow band blocking filter, which blocks all light in a determined region of the beam path of the measuring light. A piece of the spectral range on the long wave end of the spectral region to be measured is cut off with the application of a shortpass filter. In contrast to this, a reduction in the shortwave region of the spectral region to be measured is performed by a longpass filter.

BRIEF DESCRIPTION OF THE DRAWINGS

The invention allows numerous forms of embodiment. One thereof will now be explained in greater detail based on the drawing, the figures of which show as follows.

DETAILED DISCUSSION IN CONJUNCTION WITH THE DRAWINGS

Figure 1:
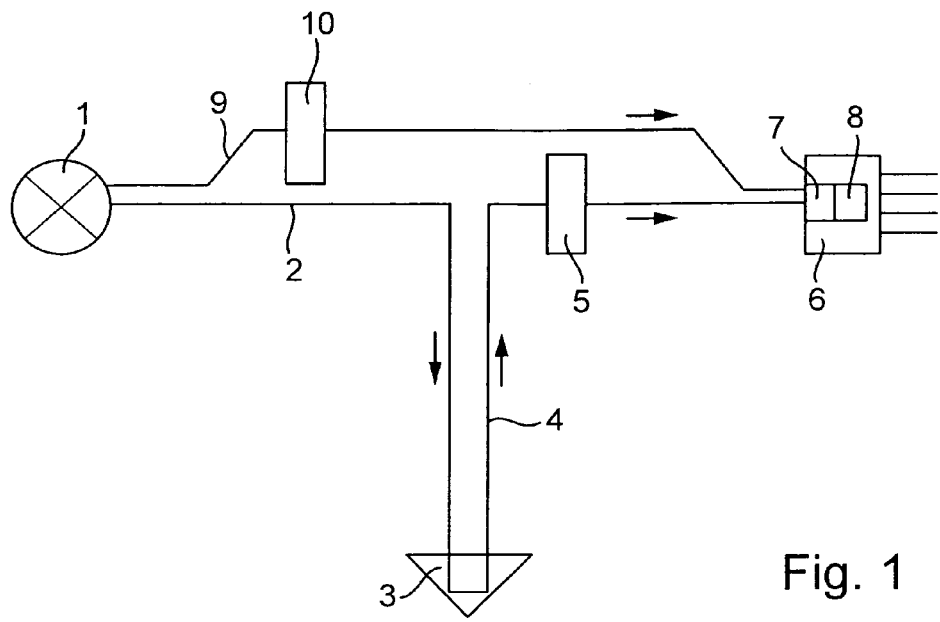
FIG. 1 is a schematic diagram of a spectrometer for performing the method of the invention.

FIG. 1 presents a schematic representation of a measurement setup for determining a spectrum in the infrared or middle infrared region; the measurement setup has a light source 1. The light beam 2 transmitted by light source 1 is fed to an optical probe 3, which is embodied in the present case as an ATR probe. An ATR probe is an immersion probe, which is immersed in a liquid medium to be measured, wherein the light beam 2, which is sent by light source 1, is completely reflected, weakened, at the interface of the ATR probe with the liquid medium to be measured, whereby the spectrum of light beam 2 is changed; the reflected light beam, as measurement beam 4, is fed through a filter 5 to the spectrometer 6. Filter 5, for example, is a notch filter, which is a narrow band blocking filter in a predetermined region of the beam of the measurement light.

A shortpass filter can also be used as an alternative to such a notch filter. In such a shortpass filter the long wave end of the spectral region to be measured is cut off.

In contrast to the shortpass filter, a longpass filter limits a section of the spectral region on the shortwave end of the spectrum. In this position in the shortwave region of the spectrum, an intensity=0 is realized in the beam path.

In addition to the measurement channel, which comprises light beam 2, probe 3, measuring beam 4 and filter 5 and which is fed to spectrometer 6, a reference channel, which extends parallel to the measurement channel 2, 3, 4, 5, is present in the measuring arrangement. A bandpass filter 10, which filters reference beam 9, which likewise emerges from light source 1, to a very narrow band, is set in this reference channel, which means that light of approximately only one wavelength passes through bandpass filter 10. This very narrowband reference beam 9 is likewise fed to the spectrometer 6.

Figure 2:
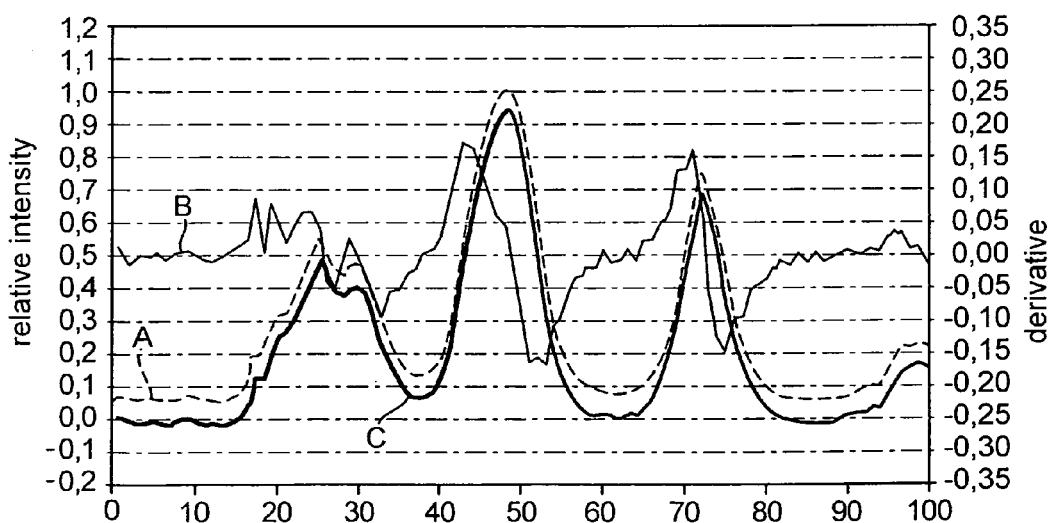
FIG. 2 is a spectra obtained by measuring a discharge with the assistance of a spectrometer of FIG. 1.

A Fabry-Perot filter 7 is arranged within spectrometer 6 and after which a pyrodetector 8 is placed. Reference beam 9 and measuring beam 4, which passes through filter 5, strike Fabry-Perot filter 7 of spectrometer 6 simultaneously. The wavelength within the optical spectrum delivered by measuring beam 4 is electrically tuned-in by means of the Fabry-Perot filter 7. In such case, the performance of the time modulation of the wavelengths occurs over a large spectral range. In such case, one obtains a differentiated spectrum; integrating this yields the absolute spectrum, except for an integration constant. Such a spectrum is presented in FIG. 2, in which curve A shows the original spectrum, which is measured from measurement beam 4 behind the ATR probe 3. Curve B shows, in such case, the spectrum, which is derived from measuring beam 4 using Fabry-Perot filter 7 and which was recorded before pyrodetector 7. Lastly, curve C shows the spectrum obtained through integration; curve C comes very near to the original spectrum of curve A.

For a difference measurement of the intensity, the electronic modulation by the Fabry-Perot filter 7 occurs between two wavelengths of the spectrum of measurement beam 4, wherein the two wavelengths can either be neighboring wavelengths of the spectrum or wavelengths of the spectrum widely remote from one another. In such case, switching occurs rapidly back and forth between the two wavelengths, wherein the resulting amplitude of the output signal of the pyrodetectors is a measure for the intensity difference of the two wavelengths. Through evaluating the phase of the measurement signal 4 it can be determined which of the two wavelengths has the higher intensity.

Ascertaining the absolute intensity is possible through a comparison measurement of the difference of the intensities with a wavelength, which is delivered by reference band 9 and whose wavelength is known, with the position of the spectrum, which is characterized by filter 5 with an intensity=0.

After establishing the integration constant, deductions about the actual absolute intensity of the spectrum can then be made.

For the comparison measurement, the reference signal 9 is coupled in. The reference signal 9 is directly conveyed from light source 1 via bandpass filters 10 to a second input of spectrometer 6. In such case, measurement signal 4, which is equipped by filter 5 with a reference point with an intensity=0, is superimposed by the reference signal 9. The central wavelength of reference signal 9 allowed through bandpass filters 10 must, in such case, lie in the region of the spectrum, where filter 5 has the transmission=0. In this way, only reference light of the wavelength used reaches the pyrodetector 8 and the omitted region in the measurement signal 4 with an intensity=0 is not completely filled by reference signal 9. Therewith remains the possibility further to obtain an absolute measurement of the intensity.

Figure 3:
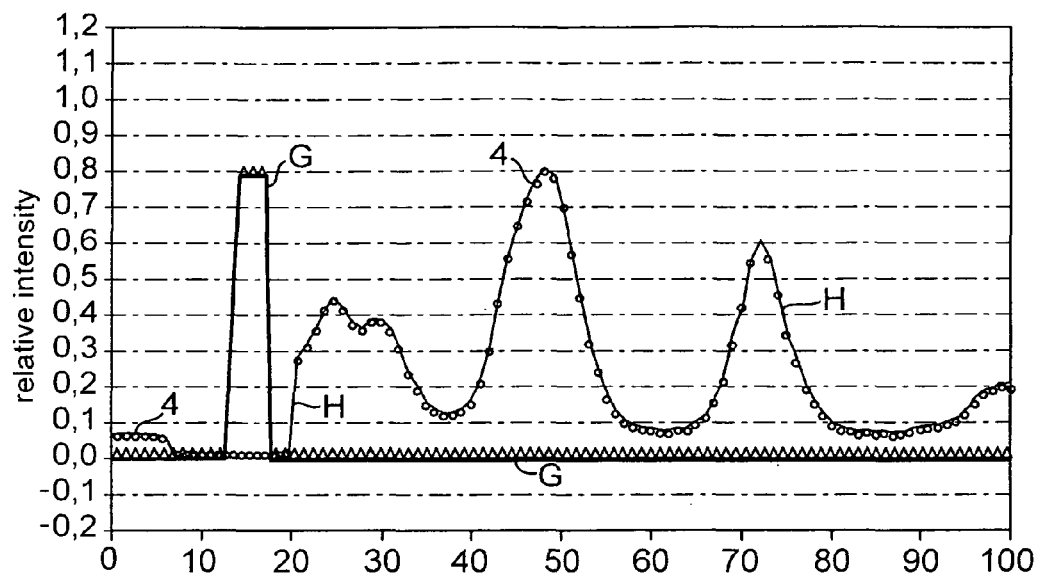
FIG. 3 is a measured spectrum with measuring and reference information.

FIG. 3 shows a measured spectrum with measurement and reference information. In such case, the relative intensity is plotted versus wavelength. The reference band G of reference signal 9 has an intensity, in such case, only in a very narrow-band wavelength range, while intensity=0 to both of its sides. The measurement signal 4, which has an intensity of zero in the region between 10 and 20 due to the use of filter 5, is identical to the measured spectrum received by pyrodetector 8 in the remaining curve of the spectrum; this is shown by the curve H. This measured spectrum characterized by curve H can, thus, be reliably evaluated by spectrometer 6, wherein information regarding the absolute intensity of the measurement spectrum can be realized. With this arrangement the light power of light source 1 can be measured. Changes to the light power of light source 1 can, thus, be registered and compensated.

Figure 4:
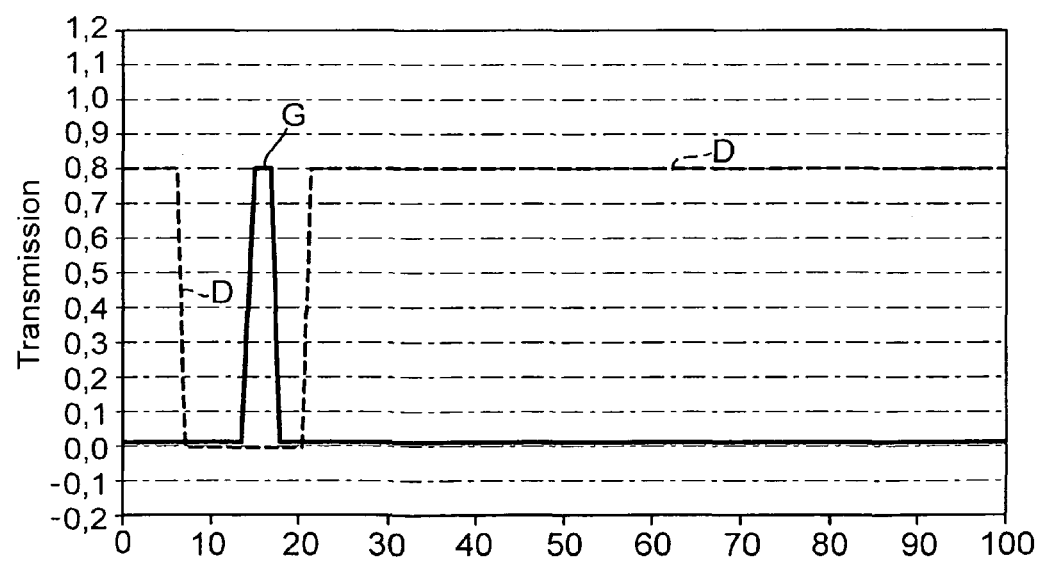
FIG. 4 is a first example of an embodiment with a notch filter in the measurement channel.
Figure 5:
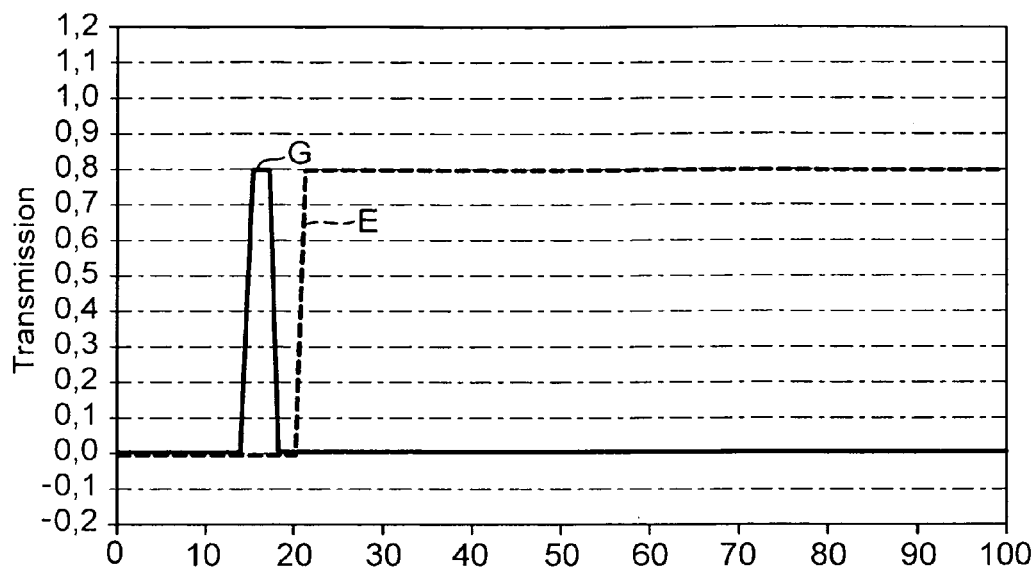
FIG. 5 is a second example of an embodiment with a shortpass filter in the measurement channel.
Figure 6:
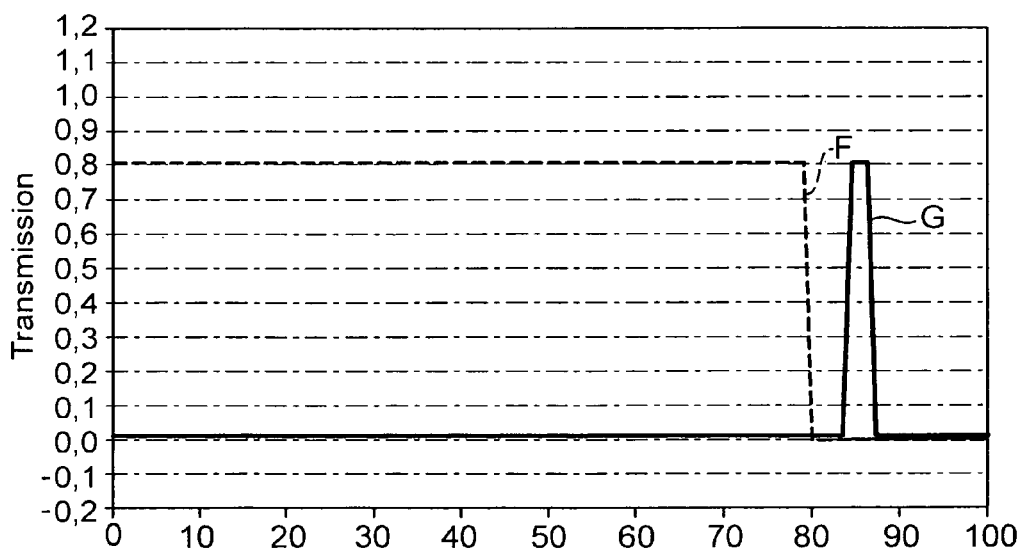
FIG. 6 is a third example of an embodiment with a longpass filter in the measurement channel.

Signal curves of the filters, which impress a wavelength with an intensity=0 in the measurement signal 4 of the ATR probe, and the signal curve of the reference signal are presented in FIGS. 4, 5 and 6. The wavelength signal let through by the respective filter is characterized by curve D for the notch filter in FIG. 4, curve E for the shortpass filter in FIG. 5 and curve F for the longpass filter in FIG. 6. The narrowband reference band of reference signal 9 is marked by the character G. As evident from all three of FIGS. 4, 5, 6, the reference band G, in such case, is always arranged in the region of the spectral region where the intensity of measuring light 4 equals zero. Thus, a reliable association of the intensity to the wavelength of the spectral region of the measuring light 4 is realized.

The invention claimed is:

1. A method for measuring a spectrum, advantageously in the infrared region, in which a light beam impinges on an optical sensor, which is in contact with a medium to be measured, comprising the steps of:
   transmitting a measurement beam by the optical sensor, which beam is a measurement beam changed by the medium to be measured;
   feeding the measurement beam to a pyrodetector, which issues output signals corresponding to the spectrum;
   modulating the intensity of the measurement beam before impinging on the pyrodetector; and
   intensity modulation of the measurement beam occurs by tuning-in wavelengths contained in the optical spectrum of the measurement beam.

2. The method as claimed in claim 1, wherein:
   the light signal is transmitted without modulation.

3. The method as claimed in claim 2, wherein:
   either only a narrow first region surrounding a wavelength of the optical spectrum to be detected or a wider second region surrounding a wavelength of the optical spectrum to be detected is tuned.

4. The method as claimed in claim 1, further comprising the steps of:
   determining a difference from the intensities of two wavelengths measured by the pyrodetector; and
   using the difference for ascertaining an integration constant.

5. The method as claimed in claim 1, further comprising the step of:
   producing a position with zero intensity in the wavelength spectrum of the measurement beam.

6. The method as claimed in claim 5, wherein:
   a narrow band reference signal impinges on the pyrodetector, preferably simultaneously with the measurement beam.

7. The method as claimed in claim 6, wherein:
   the reference signal is formed by an additional light beam, which is bandpass filtered before impinging on pyrodetector.

8. An apparatus for measuring a spectrum, advantageously in the infrared region, comprising:
   an optical sensor;
   a light source which transmits a light beam which impinges on said optical sensor, which is in contact with a medium to be measured;
   a pyrodetector; and
   an intensity modulator wherein:
   said optical sensor transmits a measurement beam changed by the medium to be measured and the measurement beam is fed to said pyrodetector, which issues an output signal corresponding to the spectrum;
   said intensity modulator changes the intensity of measurement beam and is arranged before said pyrodetector; and
   said intensity modulator comprises a filter with tunable wavelength.

9. The apparatus as claimed in claim 8, wherein:
   characterized said filter is a Fabry-Perot filter with an electrically tunable wavelength, said filter being arranged either before spectrometer or together with the pyrodetector in the spectrometer.

10. The apparatus as claimed in claim 8, wherein:
    a notch filter, a shortpass filter or a longpass filter is arranged in the measurement beam before spectrometer.

* * * * *